US008887625B2

(12) United States Patent
Satoh et al.

(10) Patent No.: US 8,887,625 B2
(45) Date of Patent: Nov. 18, 2014

(54) HYDROGEN ADDING EQUIPMENT FOR LIVING ORGANISM APPLICABLE FLUID

(71) Applicant: MIZ Co., Ltd., Kanagawa (JP)

(72) Inventors: Fumitake Satoh, Kanagawa (JP); Tomoki Seo, Kanagawa (JP); Ryosuke Kurokawa, Kanagawa (JP); Bunpei Satoh, Kanagawa (JP)

(73) Assignee: MIZ Co., Ltd., Kanagawa (JP)

( * ) Notice: Subject to any disclaimer, the term of this patent is extended or adjusted under 35 U.S.C. 154(b) by 0 days.

(21) Appl. No.: 13/711,471

(22) Filed: Dec. 11, 2012

(65) Prior Publication Data

US 2013/0098250 A1 Apr. 25, 2013

Related U.S. Application Data

(63) Continuation of application No. PCT/JP2011/073808, filed on Oct. 17, 2011.

(30) Foreign Application Priority Data

Oct. 18, 2010 (JP) ................................. 2010-233312

(51) Int. Cl.
| | | |
|---|---|---|
| A23F 3/00 | (2006.01) | |
| A23L 2/54 | (2006.01) | |
| C02F 1/68 | (2006.01) | |
| C01B 3/08 | (2006.01) | |
| C02F 1/70 | (2006.01) | |

(52) U.S. Cl.
CPC ... A23L 2/54 (2013.01); C02F 1/68 (2013.01); C01B 3/08 (2013.01); C02F 1/705 (2013.01); Y02E 60/36 (2013.01)
USPC ........................................................ 99/323.1

(58) Field of Classification Search
CPC ............... A23L 2/54; C01B 3/08; C02F 1/68; C02F 1/705; Y02E 60/36
USPC ........ 99/275, 279, 323, 323.1, 317, 321, 322; 261/100–102; 210/749, 198.1, 202, 210/206, 266, 501
See application file for complete search history.

(56) References Cited

U.S. PATENT DOCUMENTS

| | | |
|---|---|---|
| 2002/0048548 A1 | 4/2002 | Chaklader |
| 2005/0121399 A1 | 6/2005 | Hayashi et al. |

(Continued)

FOREIGN PATENT DOCUMENTS

| | | |
|---|---|---|
| DE | 102006035629 | 6/2007 |
| JP | 2004-344783 A | 12/2004 |

(Continued)

OTHER PUBLICATIONS

English Language Translation of JP2006255613 (Applicant in IDS).*

(Continued)

*Primary Examiner* — Dana Ross
*Assistant Examiner* — Joseph Iskra
(74) *Attorney, Agent, or Firm* — Muncy, Geissler, Olds & Lowe, P.C.

(57) ABSTRACT

Hydrogen gas is added into living organism applicable fluid substantially without changing constituents of the living organism applicable fluid by reacting a hydrogen generating system and a generating-purpose water, wherein the hydrogen generating system contains metal aluminum, which is a food additive, as a hydrogen generating agent and calcium oxide or calcium hydroxide, which is also a food additive, as a hydrogen generating reaction accelerator such that the hydrogen generating agent and the hydrogen generating reaction accelerator are adjacent to each other.

5 Claims, 1 Drawing Sheet a: separator
b: container
c: living organism applicable fluid
d: porous container

(56) References Cited

U.S. PATENT DOCUMENTS

| | | |
|---|---|---|
| 2007/0128104 A1 | 6/2007 | Hayashi et al. |
| 2007/0181853 A1 | 8/2007 | Torimoto et al. |
| 2008/0311225 A1 | 12/2008 | Shiga |
| 2009/0098424 A1* | 4/2009 | Nakai et al. ............ 429/19 |
| 2012/0087990 A1 | 4/2012 | Shiga |
| 2012/0225010 A1* | 9/2012 | Boyle et al. ............ 423/657 |

FOREIGN PATENT DOCUMENTS

| | | | |
|---|---|---|---|
| JP | 2006-255613 A | | 9/2006 |
| JP | 2007-167696 A | | 7/2007 |
| JP | 2007167696 | * | 7/2007 |
| JP | 2007-209854 A | | 8/2007 |
| JP | 2009-173532 A | | 8/2009 |
| JP | 2010-274236 A | | 12/2010 |
| JP | 2009-131790 | | 12/2012 |
| WO | WO0208118 | * | 1/2002 |
| WO | WO 2005/097491 | | 10/2005 |
| WO | WO 2007/089549 | | 8/2007 |
| WO | WO2007089549 | * | 8/2007 |
| WO | WO2010/092770 | | 8/2010 |
| WO | WO 2010/103894 | | 9/2010 |

OTHER PUBLICATIONS

Ishibashi et al., "Consumption of water containing a high concentration of molecular hydrogen reduces oxidative stress and disease activity in patients with rheumatoid arthritis: an open-label pilot study", Medical Gas Research, 2012, 8 pages, vol. 2:27.

* cited by examiner

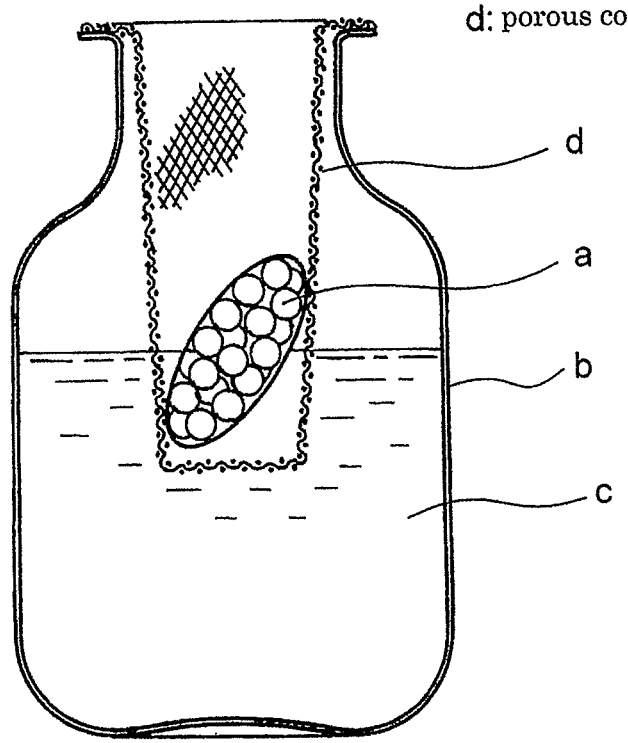
a: separator
b: container
c: living organism applicable fluid
d: porous container

HYDROGEN ADDING EQUIPMENT FOR LIVING ORGANISM APPLICABLE FLUID

BACKGROUND OF THE INVENTION

1. Field of the Invention

The present invention relates to a hydrogen adding equipment for living organism applicable fluid.

2. Description of the Related Art

As a method of producing living organism applicable hydrogen-contained fluid, known in the art are a method using a hydrogen water electrolytically generating apparatus for household use and a method causing metal pieces of metal magnesium as a hydrogen generating agent to contact with living organism applicable fluid (Japanese Patent Application Publication No. 2007-167696).

PRIOR ART DOCUMENTS

Patent Document(s)

[Patent Document 1] Japanese Patent Application Publication No. 2007-167696

SUMMARY OF THE INVENTION

Problems to be Solved by the Invention

In the case of obtaining living organism applicable hydrogen-contained fluid using hydrogen generating agent, the hydrogen generating agent may possibly change properties of the living organism applicable fluid when dissolving hydrogen molecules into the living organism applicable fluid. For example, if the hydrogen generating agent is metal magnesium, then magnesium ions are dissolved into the living organism applicable fluid to shift the pH thereof toward alkaline side when generating hydrogen.

However, it is not desirable in general to change, before and after the hydrogen generating reaction, constituents of the living organism applicable fluid having been already made up naturally or artificially. The change in constituents may in turn lead to even altering the flavor of living organism applicable fluid, such as tea and mineral water.

Therefore, an equipment for producing living organism applicable hydrogen-contained fluid is desired which does not change constituents of living organism applicable fluid.

Besides, only "food additives" are officially permitted as additives allowed for contacting with articles of food under the Food Sanitation Act. Accordingly, if living organism applicable hydrogen-contained fluid is obtained by a method of causing magnesium or hydrogenated metal, which is not permitted as such food additives, to directly contact with living organism fluid, then the method involves problems including noncompliance with the Food Sanitation Act.

Means for Solving the Problems

Problems are solved by adding hydrogen gas into living organism applicable fluid substantially without changing constituents of the living organism applicable fluid by reacting a hydrogen generating system and a generating-purpose water, wherein the hydrogen generating system contains metal aluminum, which is a food additive, as a hydrogen generating agent and calcium oxide or calcium hydroxide, which is also a food additive, as a hydrogen generating reaction accelerator such that the hydrogen generating agent and the hydrogen generating reaction accelerator are adjacent to each other.

Advantageous Effect of the Invention

By supplying hydrogen into the living organism applicable fluid using such means, living organism applicable hydrogen-contained fluid can be obtained without substantially changing properties of the living organism applicable fluid. Moreover, using such means also allows high concentration or supersaturated hydrogen beverages to be easily produced without altering the flavor of any beverage regardless of locations, such as home, workplace, street, and storefront.

BRIEF DESCRIPTION OF THE DRAWINGS

FIG. 1 is a front elevational view illustrating a hydrogen adding equipment maintained in the gas phase according to one embodiment of the present invention.

DESCRIPTION OF THE PREFERRED EMBODIMENTS

Hereinafter, embodiments of the present invention will be described.

Living organism applicable fluid in the present invention is a fluid to be applied to living organisms, such as water or water solution, which is an objective to be dissolved therein with hydrogen using the present invention. Examples of living organism applicable fluid include water as well as softdrinks and beverages such as tea and coffee. Living organism applicable hydrogen-contained fluid to be obtained by dissolving hydrogen into the living organism applicable fluid is applied to living organisms via inhalation (atomization), drinking, injection, and the like, but is not limited thereto. It is considered that an active constituent of the living organism applicable hydrogen-contained fluid and high-concentration or supersaturated living organism applicable hydrogen-contained fluid is hydrogen and the functionality thereof is primarily inhibition of oxidant stress, but the functionality is not limited thereto.

Hydrogen generating agent in the present invention is a substance which generates hydrogen. Examples of hydrogen generating agent include metals having higher ionization tendency than hydrogen, hydrogenated compounds including metal hydride, and other substances. In consideration of the safety of the resulting reaction products and the Food Sanitation Act, it is preferred to use metals having higher ionization tendency than hydrogen (iron, aluminum, nickel, and cobalt), which are food additives. Among them, metal aluminum is preferably used from the viewpoints of aesthetic aspect, cost, and safety in handling.

Hydrogen generating reaction accelerator in the present invention is an agent which accelerates the hydrogen generating reaction of the hydrogen generating agent contained in the hydrogen generating system. Acid, alkaline agent or other agent may be used as the hydrogen generating reaction accelerator. As acid, it is preferred to use, such as, but not limited to, acid which generates solid precipitations after the reaction or solid acid such as ion-exchange resin. In addition to acid, alkaline agent such as calcium hydroxide, calcium oxide or anion-exchange resin may also be used when amphoteric metal such as aluminum or zinc is used as the hydrogen generating agent. Among them, it is preferred to use alkaline agent, such as calcium hydroxide (hydrated lime), calcined lime (calcium oxide), burnt calcium, magnesium oxide, magnesium hydroxide, or anion-exchange resin, which is a food additive. As will be described later, such a hydrogen generating reaction accelerator that reacts with metal, such as aluminum, which has higher ionization tendency than hydrogen and which is a food additive, to generate precipitations is suitable for objects of the present invention of substantially not changing properties of the living organism applicable fluid, because the hydrogen generating reaction accelerator suppresses metal ions of the metal from re-dissolving after the hydrogen generating reaction.

In addition, it is preferred that, in order to suppress time degradation of the hydrogen generating agent, the hydration number and the water content ratio of the hydrogen generating reaction accelerator, such as an appropriate acid or alkaline agent, contained in the hydrogen generating system are lower. More specifically, with respect to the hydration number, it is desirable to be trihydrate or lower, preferably dihydrate or lower, more preferably monohydrate or lower, and most preferably nonhydrate or anhydride. It is also desirable that the water content ratio is 40 weight % or less, preferably 30 weight % or less, more preferably 20 weight % or less, and most preferably 15 weight % or less.

Generating-purpose water in the present invention is a liquid for causing hydrogen gas to be generated through contacting with a hydrogen generating system. Examples of such generating-purpose water include tap water, clarified water, ion-exchanged water, purified water, pure water, RO water, and the like, but are not limited thereto. The living organism applicable fluid in itself, which is an objective to be added therein with hydrogen by the hydrogen generating system, may also be used as the generating-purpose water. Regardless of contained components, hardness, and liquid properties, any liquid including water may be used as the generating-purpose water in the present invention.

With respect to a target of the usage of the generating-purpose water, assuming that the weight of the hydrogen generating system is 1.0, it is desirable that the weight ratio is 0.0112, preferably within the range of 0.05 to 6, more preferably within the range of 0.1 to 3, and most preferably within the range of 0.1 to 2.

Note that the hydrogen generating system includes metal aluminum and calcium oxide or calcium hydroxide, and if the generating-purpose water is caused to react therewith, then the metal aluminum may react with the calcium hydroxide in accordance with the following formulae 1 and 2, thereby generating hydrogen and forming as a by-product an alumina cement (calcium aluminate) to be rapidly solidified.

$$CaO + H_2O \rightarrow Ca(OH)_2 \quad \text{(Formula 1)}$$

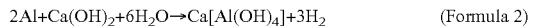

$$2Al + Ca(OH)_2 + 6H_2O \rightarrow Ca[Al(OH)_4] + 3H_2 \quad \text{(Formula 2)}$$

Since this reaction is an irreversible reaction, the re-dissolution of aluminum ions and hydroxide ions from alumina cement to the living organism applicable fluid is restrictive, so that there scarcely occurs the dissolution of metal ions into the living organism applicable fluid or the variation in pH, therefore substantially not changing constituents of the living organism applicable fluid.

Moreover, alumina cement is a substance having fire resistance thereby to act as a fireproofing agent or a fireproofing layer against ignitible metal aluminum remaining after the hydrogen generating reaction, if in a condition where metal aluminum and calcium oxide or calcium hydroxide are adjacent to each other in the hydrogen generating system.

In the present invention, concepts of being in a condition where metal aluminum and calcium hydroxide are adjacent to each other include a condition where metal aluminum and calcium hydroxide are mixed and then made as being tablets by tablet machinery or solidified, or a condition where they are mixed and filled into one or more separators. Such tablets or solidified materials may further be held in one or more separators. Moreover, by making the hydrogen generating system be tablets or solidified, metal aluminum may be prevented from the risk of dust explosion.

Note that the one or more separators in the present invention are to separate the hydrogen generating system from the living organism applicable fluid and to maintain a condition where the hydrogen generating agent and the hydrogen generating reaction accelerator are adjacent to each other, and when the separators are put in the living organism applicable fluid, a part of the living organism applicable fluid is to be introduced as the generating-purpose water into the separators. Accordingly, it is desirable that the separators are capable of releasing hydrogen gas and have gas-permeable films or other materials which are allowed to be permeated with appropriate amount of water. Note also that the gas-permeable films in the present invention are not limited in their materials (fabric, paper, plastic, etc) and thicknesses, while the water-permeability and the water-retentivity of gas-permeable films to be used are not necessary to be too high, because if the introduced amount of the generating-purpose water is unduly large, the amount of aluminum ions and hydroxide ions to flow out after the hydrogen generating reaction increase in proportion thereto. More specifically, examples of gas-permeable films to be preferably used in the present invention may include films produced using high molecular materials, such as polyester, polyethylene and polypropylene, and even nonwoven fabrics, synthetic resin films or other materials, which have possibly been subjected to water repellent finishing during production or processing. For example, separators employing as gas-permeable films nonwoven fabrics having been subjected to water repellent finishing, such as Tyvek available from DuPont, have a feature of not substantially changing constituents of the living organism applicable fluid, because such separators have low water-permeability and low water-retentivity thereby being hard to introduce the external generating-purpose water, while on the other hand the generating-purpose water having been once introduced into the separators is repelled at gas-permeable film surfaces in the separators, so that the generating-purpose water contained therein with metal ions and hydroxide ions scarcely flows out from the separators.

Such gas-permeable films may be included as parts of separators, or whole of separators may be configured of gas-permeable films. If whole of separators are configured of gas-permeable films, then the separators are usually in a form of bag-like shape, but the shape of separators is not limited thereto.

Note that such separators also cause metal aluminum and calcium hydroxide or calcium oxide to be physically adjacent to each other thereby efficiently progressing the hydrogen generating reaction, and are thus suitable for the object of avoiding the dissolution of aluminum ions and hydroxide ions owing to the formation of alumina cement as heretofore described.

Note further that the equipment according to the present invention may be put in the living organism applicable fluid, or held in the air space of a container stored therein with the living organism applicable fluid. In either case, airtightly closing the container (holding the equipment in a closed container) is preferred for facilitating the dissolution of hydrogen gas into the living organism applicable fluid. Moreover, shaking such a closed container in which the equipment is held is further preferred for facilitating the dissolution of hydrogen gas into the living organism applicable fluid.

Note still further that, in the case where the equipment according to the present invention is held in the air space of the container for the living organism applicable fluid, a configuration is preferred to be devised, as shown in FIG. 1, such that when the hydrogen generating system stored in separators (a) is inserted from the mouth of a container (b), the system is not to fully immersed into living organism applicable fluid (c) owing to a part thereof being engaged with the mouth of the container or other means. To this end, the hydrogen generating system stored in the separators is, such as, but not limited to, further stored in a porous container (d) having a flange at the upper end thereof or in any appropriate container. Such a configuration allows a part of the living organism applicable fluid to pass through pores of the porous container to be introduced into the separators, and the hydrogen generating reaction is thus performed.

In this case, the closed container in the present invention is intended to include a container which is devised not to expose the contents in the container to the air. Examples of the closed container include containers with lids, such as PET bottles and aluminum bottles with caps. It is desirable that the container has a portable form and volume in order for a person to easily shake it in his/her hand. It is also desirable that the container is of 2 L or less, preferably 1 L or less, and most preferably 0.5 L or less, but not limited thereto.

Preferred materials for the closed container are to have low hydrogen permeability. As the hydrogen permeability is lower, the generated hydrogen is hard to escape from the container system.

The hydrogen permeability of the closed container in the present invention is measured as follows. That is, with reference to the method described in Patent Application No. 2009-221567 or the like, hydrogen dissolved water is prepared to stably keep approximately the saturated concentration (1.6 ppm at 20 degrees C. and 1 atm) with the volume of 20 times of the inner volume of a closed container as an object to be measured, and the closed container is then immersed during 5 hours in the hydrogen dissolved water after being fully filled with clarified water (charcoal-treated water, such as Fujisawa city tap water (tap water available from Fujisawa city water-service) treated to pass through a charcoal column).

Thereafter, the dissolved hydrogen concentration in the clarified water is measured, wherein the container of lower hydrogen permeability in the present invention involves a closed container with dissolved hydrogen concentration of 1,000 ppb or lower, preferably 500 ppb or lower, more preferably 100 ppb or lower, and most preferably 10 ppb or lower.

It is desirable that the closed container has a pressure-proof property capable of resisting the increasing of the inner pressure due to the generation of hydrogen. Specifically, it is desirable to be a pressure-proof container capable of resisting the inner pressure of 0.11 MPa as absolute pressure, preferably 0.4 MPa, more preferably 0.5 MPa, and most preferably 0.8 MPa. A PET bottle for carbonated drink or any appropriate bottle may be preferably used. It is also desirable that the closed container comprises at the mouth thereof a mechanism for releasing the pressure (vent slot) midway through opening the cap for the purpose of safety opening.

The shaking in the present invention is to give a physical impact or shock to the closed container thereby replacing the dissolved gas such as dissolved oxygen in the living organism applicable fluid with hydrogen gas while contacting the living organism applicable fluid and the gas-phase hydrogen with each other in the closed container. The shaking in the present invention involves natural shaking using hand or hands as well as artificial shaking using a machine. Examples of such artificial shaking include shaking by using a shaking machine, an agitator, an ultrasonic generator, and other apparatuses.

Moreover, in order for hydrogen gas to be further accumulated in the gas phase in the closed container, it is desirable to start the shaking after 1 minute has elapsed, preferably 2 minutes, more preferably 4 minutes, furthermore preferably 8 minutes, and most preferably 10 minutes, from the time when the hydrogen adding equipment according to the present invention was disposed in the closed container.

Note that an exemplary case of the natural shaking in the present invention is as follows. That is, the shaking is performed by a Japanese man of 30's having an average physical size, who holds the middle portion of the closed container by his dominant hand and moves only the wrist to shake it such that the cap forms into an arch above the wrist with a pace of 2 strokes per second, total 120 strokes.

Further, in order to accelerate the dissolution of the high-pressure and high-concentration hydrogen gas into the living organism applicable fluid, it is desirable that the time period of the shaking is 5 seconds or longer for the natural shaking, preferably 10 seconds or longer, more preferably 15 seconds or longer, and still preferably 30 seconds or longer.

Moreover, it is preferred that the shaking is such that, when performing the shaking after leaving in stationary condition the hydrogen adding equipment for living organism applicable fluid according to the present invention in the living organism applicable fluid during 10 minutes, the dissolved hydrogen concentration in the living organism applicable fluid is enhanced twice or higher of the dissolved hydrogen concentration before the shaking, preferably 3 times or higher, more preferably 4 times or higher, 5 times or higher, 6 times or higher, 7 times or higher, 8 times or higher and 9 times or higher in this order, and further preferably 10 times or higher.

Furthermore, it is preferred that the inner pressure in the closed container before the shaking is equal to or higher than the atmosphere pressure in order to obtain higher concentration living organism applicable hydrogen-contained fluid, such as supersaturated living organism applicable hydrogen-contained fluid with 1.6 ppm or higher. The solubility of hydrogen molecules to the living organism applicable fluid increases as the inner pressure loaded by the generated hydrogen molecules to the closed container increases, and exceeds the solubility at the normal temperature and pressure in due time. The reason why the closed container storing the hydrogen generating system is left for a while for example in the examples as will be described later is to pressurize the closed container from the inside by the generated hydrogen gas, and also to allow for appropriately shaking the closed container under the increased pressure thereby further accelerating the dissolution of the hydrogen molecules to the living organism applicable hydrogen-contained fluid.

Besides, it is desirable that the average grain diameter of the hydrogen generating agent such as metal aluminum in the present invention is a diameter which is enough not to pass those grains through the gas-permeable films and which enables to increase the activity by microparticulation. For example, it is desirable that the average grain diameter of the hydrogen generating agent is 3,000 μm or less, preferably 1,000 μm or less, more preferably 500 μm or less, and most preferably 250 μm or less. Further, in order to reduce the risk of dust explosion of metal aluminum, it is desirable that the average grain diameter for 50% or more thereof is 150 μm or more. Thus, the optimum grain size is appropriately determined in consideration of the increase in activity by microparticulation and the relevant possibility of dust explosion.

In the case where the hydrogen generating system in the present invention uses metal aluminum as the hydrogen generating agent and calcium oxide or calcium hydroxide as the hydrogen generating reaction accelerator, the weight compounding ratio of metal aluminum to the total weight of both materials is desirable to be 55 weight % or more and 99 weight % or less, preferable 65 weight % or more and 95 weight % or less, and further preferably 75 weight % or more and 90 weight % or less.

Concepts of the living organism applicable high concentration hydrogen-contained fluid in the present invention include a living organism applicable hydrogen-contained fluid of which the dissolved hydrogen concentration in the fluid is 0.01 ppm or more, preferably 0.1 ppm or more, and more preferably 1.0 ppm or more. Concepts of the living organism applicable supersaturated hydrogen-contained fluid in the present invention involve a situation where the dissolved hydrogen concentration is higher than or equal to the degree of solubility at ordinary temperatures and pressures, and include a living organism applicable high concentration hydrogen-contained fluid of 1.6 ppm or more, 2.0 ppm or more, 3.0 ppm or more, 4.0 ppm or more, 5.0 ppm or more, 6.0 ppm or more, 7.0 ppm or more, 8.0 ppm or more, 9.0 ppm or more, and 10.0 ppm or more.

Note that the conditions of not substantially changing the constituents of the living organism applicable fluid in the present invention include, such as, but not limited to, satisfying at least either of not changing the metal ion concentration related to the metal used as the hydrogen generating agent or not changing the pH.

Here, the conditions of not changing the metal ion concentration related to the metal used as the hydrogen generating agent include the following cases, but is not limited thereto.

Such cases include a case where the metal ion concentration (aluminum ion concentration when the equipment according to the present invention uses aluminum as the hydrogen generating agent, for example) in the living organism applicable hydrogen-contained fluid of which the raw water is a certain organism applicable fluid is within an allowable range, such as, from (metal ion concentration of the raw water minus 15 ppm) to (metal ion concentration of the raw water plus 15 ppm), preferably from (metal ion concentration of the raw water minus 10 ppm) to (metal ion concentration of the raw water plus 10 ppm), more preferably from (metal ion concentration of the raw water minus 5 ppm) to (metal ion concentration of the raw water plus 5 ppm), furthermore preferably from (metal ion concentration of the raw water minus 3 ppm) to (metal ion concentration of the raw water plus 3 ppm), and most preferably from (metal ion concentration of the raw water minus 1 ppm) to (metal ion concentration of the raw water plus 1 ppm).

Alternatively, such cases may include a case where a PET bottle for carbonated drink (about 530 cc volume when filled with full water to the mouth) is substantially filled with 515 cc of living organism applicable fluid as being clarified water obtained by dechlorination treating for tap water (clarified water such as obtained by treating Fujisawa city tap water to pass through a charcoal column), the producing equipment for living organism applicable hydrogen-contained fluid according to the present invention is disposed in the living organism applicable fluid, the bottle is left to be laid flat during 10 minutes, and immediately after performing typical and natural shaking (holding the middle portion of the PET bottle by one's dominant hand and moving only the wrist such that the cap forms into an arch above the wrist with a pace of 2 strokes per second, total 120 strokes) for the fluid, the metal ion concentration in the fluid related to the metal used as the hydrogen generating agent in the producing equipment (aluminum ion concentration when the equipment according to the present invention uses aluminum as the hydrogen generating agent, for example) is within an allowable range, such as, from (metal ion concentration of the raw water minus 15 ppm) to (metal ion concentration of the raw water plus 15 ppm), preferably from (metal ion concentration of the raw water minus 10 ppm) to (metal ion concentration of the raw water plus 10 ppm), more preferably from (metal ion concentration of the raw water minus 5 ppm) to (metal ion concentration of the raw water plus 5 ppm), furthermore preferably from (metal ion concentration of the raw water minus 3 ppm) to (metal ion concentration of the raw water plus 3 ppm), and most preferably from (metal ion concentration of the raw water minus 1 ppm) to (metal ion concentration of the raw water plus 1 ppm).

Here, the conditions of not changing the pH include the following cases, but is not limited thereto.

Such cases include a case where the pH in the living organism applicable hydrogen-contained fluid of which the raw water is a certain organism applicable fluid is within an allowable range, such as, from (pH of the raw water minus 3.0) to (pH of the raw water plus 3.0), preferably from (pH of the raw water minus 2.0) to (pH of the raw water plus 2.0), more preferably from (pH of the raw water minus 1.0) to (pH of the raw water plus 1.0), and most preferably from (pH of the raw water minus 0.5) to (pH of the raw water plus 0.5).

Alternatively, such cases may include a case where a PET bottle for carbonated drink (about 530 cc volume when filled with full water to the mouth) is substantially filled with 515 cc of living organism applicable fluid as being clarified water obtained by dechlorination treating for tap water and having pH of approximately 7.0 to 7.8 (clarified water such as obtained by treating Fujisawa city tap water to pass through a charcoal column), the producing equipment for living organism applicable hydrogen-contained fluid according to the present invention is disposed in the living organism applicable fluid, the bottle is left to be laid flat during 10 minutes, and immediately after performing typical and natural shaking (holding the middle portion of the PET bottle by one's dominant hand and moving only the wrist such that the cap forms into an arch above the wrist with a pace of 2 strokes per second, total 120 strokes) for the fluid, the pH of the fluid is within an allowable range, such as, from (pH of the raw water minus 3.0) to (pH of the raw water plus 3.0), preferably from (pH of the raw water minus 2.0) to (pH of the raw water plus 2.0), more preferably from (pH of the raw water minus 1.0) to (pH of the raw water plus 1.0), and most preferably from (pH of the raw water minus 0.5) to (pH of the raw water plus 0.5).

EXAMPLES

Hereinafter, examples of the present invention will be described. Note that, when there is no particular explanation in the present application, various gauges used for measuring various physicality values are as follows: pH meter (including temperature indicator) manufactured by Horiba, Ltd. (main body type: D-13, probe type: 9620-10D); and DH meter (dissolved hydrogen meter) manufactured by DKK-Toa Corporation (main body type: DHDI-1, electrode (probe) type: HE-5321, transponder type: DHM-F2).

Aluminum ion concentration was measured by the aluminon method using water quality analyzer DR/4000 (manufactured by HACH Company).

Example 1

The hydrogen generating system was obtained by mixing metal aluminum grains (grain diameter: 53 to 150 μm, 80% up) (Wako Pure Chemical Industries, Ltd., hereinafter the same applies) and calcium hydroxide (Wako Pure Chemical Industries, Ltd., hereinafter the same applies). The obtained hydrogen generating system contained metal aluminum grains 85 weight % and calcium hydroxide 15 weight %.

The hydrogen generating system 0.8 g was enclosed and heat sealed in nonwoven fabric (Precise Regular C5160: Asahi Kasei Corporation). A PET bottle for carbonated drink (about 530 cc volume when filled with full water to the mouth) was substantially filled with about 515 cc of Fujisawa city tap water, and the hydrogen generating system with nonwoven fabric was then put into the Fujisawa city tap water. Five sets of the same were prepared.

Respective bottles were closed with their caps and left during 10 minutes, 30 minutes, 1 hour, 2 hours, and 15 hours.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Subsequently, measurements were done for pH, dissolved hydrogen concentration (DH), and aluminum (Al) ion concentration of each content fluid.

Reference Example 1

Measurements were done for pH and aluminum (Al) concentration of the Fujisawa city tap water used for Example 1.

Example 2

The hydrogen generating system was obtained by homogeneously dispersing metal aluminum grains and calcium hydroxide. The obtained hydrogen generating system contained metal aluminum grains 85 weight % and calcium hydroxide 15 weight %.

The hydrogen generating system 0.8 g was enclosed and heat sealed in nonwoven fabric (Tyvek 1073B: DuPont-Asahi Flash Spun Products Co., Ltd.). A PET bottle for carbonated drink (about 530 cc volume when filled with full water to the mouth) was substantially filled with about 515 cc of Fujisawa city tap water, and the hydrogen generating system with nonwoven fabric was then put into the Fujisawa city tap water. Five sets of the same were prepared.

Respective bottles were closed with their caps and left during 10 minutes, 30 minutes, 1 hour, 2 hours, and 15 hours.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Subsequently, measurements were done for pH, dissolved hydrogen concentration (DH), and aluminum (Al) ion concentration of each content fluid.

Reference Example 2

Measurements were done for pH and aluminum (Al) concentration of the Fujisawa city tap water used for Example 2.

Comparative Example 1

Mixed power 0.8 g was prepared to contain metal aluminum grain 85 weight % and calcium hydroxide 15 weight %. A PET bottle for carbonated drink (about 530 cc volume when filled with full water to the mouth) was substantially filled with about 515 cc of Fujisawa city tap water, and the mixed power was then put into the Fujisawa city tap water.

The bottle was closed with its cap and left during 10 minutes.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Subsequently, measurements were done for pH, dissolved hydrogen concentration (DH), and aluminum (Al) ion concentration of the content fluid.

Example 3

The hydrogen generating system was obtained by mixing metal aluminum grains and calcium hydroxide. The obtained hydrogen generating system contained metal aluminum grains 85 weight % and calcium hydroxide 15 weight %.

The hydrogen generating system 0.8 g was enclosed and heat sealed in nonwoven fabric (Tyvek 1073B: DuPont-Asahi Flash Spun Products Co., Ltd.) and stored in a tubular porous container (bottom: circular with diameter of about 14 mm, height: about 58 mm). A PET bottle for carbonated drink (about 530 cc volume when filled with full water to the mouth) was substantially filled with about 515 cc of Fujisawa city tap water, the porous container was then inserted into the PET bottle mouth while the flange surrounding the upper end of the porous container was engaged with the mouth so as not immerse the porous container into water, and the bottle was closed with the cap.

Thereafter, the bottle was left to be laid flat during 10 minutes so as to cause the porous container to fully contact the water, and one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Subsequently, measurements were done for pH, dissolved hydrogen concentration (DH), and aluminum (Al) ion concentration of the content fluid.

Reference Example 3

Measurements were done for pH and aluminum (Al) concentration of the Fujisawa city tap water used for Example 3.

Example 4

The hydrogen generating system was obtained by mixing metal aluminum grains and calcium hydroxide powder. The hydrogen generating system was solidified with tableting pressure of 5 kN using a tableting machine (HANDTAB-Jr: Ichihashi Seiki Co., Ltd.). The obtained hydrogen generating system tablets contained metal aluminum grains 80 weight % and calcium hydroxide 20 weight %.

A PET bottle for carbonated drink (about 530 cc volume when filled with full water to the mouth) was substantially filled with about 515 cc of Fujisawa city tap water, and the hydrogen generating system tablets were then put into the Fujisawa city tap water. Three sets of the same were prepared.

Respective bottles were closed with their caps and left during 10 minutes, 30 minutes, and 1 hour.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Subsequently, measurements were done for pH, dissolved hydrogen concentration (DH), and aluminum (Al) ion concentration of each content fluid.

Reference Example 4

Measurements were done for pH and aluminum (Al) concentration of the Fujisawa city tap water used for Example 4.

Example 5

The hydrogen generating system was obtained by mixing metal aluminum grains and calcium hydroxide. The obtained hydrogen generating system contained metal aluminum grains 85 weight % and calcium hydroxide 15 weight %.

The hydrogen generating system 0.8 g was enclosed and heat sealed in nonwoven fabric (Tyvek 1073B: DuPont-Asahi Flash Spun Products Co., Ltd.). A PET bottle for carbonated drink (about 530 cc volume when filled with full water to the mouth) was substantially filled with about 515 cc of Fujisawa city tap water, and the hydrogen generating system with nonwoven fabric was then put into the Fujisawa city tap water. Three sets of the same were prepared.

Respective bottles were left during 10 minutes, 30 minutes, and 1 hour without being closed by caps.

Thereafter, measurement was done for dissolved hydrogen concentration (DH) of each content fluid.

Results thereof are shown as follows in Table 1.

Each hydrogen generating system 0.8 g was enclosed and heat sealed in nonwoven fabric (Precise Regular C5160: Asahi Kasei Corporation). A PET bottle for carbonated drink (about 530 cc volume when filled with full water to the mouth) was substantially filled with about 515 cc of Fujisawa city tap water, and each hydrogen generating system with nonwoven fabric was then put into the Fujisawa city tap water. Two sets of the same were prepared for each example.

Respective bottles were closed with their caps and left during 10 minutes and 30 minutes.

Thereafter, one of the present inventors (Japanese man of 30's having an average physical size) held the middle portion of the PET bottle by his dominant hand and moved only the wrist to shake it such that the cap was forming into an arch above the wrist with a pace of 2 strokes per second, total 120 strokes (total 60 seconds).

Subsequently, measurements were done for pH, dissolved hydrogen concentration (DH), and aluminum (Al) ion concentration of each content fluid.

Reference Examples 5

Measurements were done for pH and aluminum (Al) concentration of the Fujisawa city tap water used for Examples 6 to 10.

Reference Examples 6

Measurements were done for pH and aluminum (Al) concentration of the Fujisawa city tap water used for Examples 11 and 12.

Results thereof are shown as follows in Table 2.

TABLE 1

|  | Left Time | DH (ppm) | pH | Al ion (ppm) |
|---|---|---|---|---|
| Reference Example 1 | — | — | 6.91 | 0.016 |
| Example 1 | after 10 min. | 2.80 | 7.20 | 0.029 |
|  | after 30 min. | 3.60 | 7.27 | 0.135 |
|  | after 1 Hr. | 3.80 | 7.52 | 0.310 |
|  | after 2 Hrs. | 4.60 | 7.60 | 0.630 |
|  | after 15 Hrs. | 5.10 | 7.92 | 1.520 |
| Reference Example 2 | — | — | 7.00 | 0.019 |
| Comparative Example 1 | after 10 min. | 1.21 | 11.09 | 15.010 |
| Example 2 | after 10 min. | 1.60 | 6.99 | 0.017 |
|  | after 30 min. | 2.60 | 6.95 | 0.021 |
|  | after 1 Hr. | 1.70 | 6.95 | 0.018 |
|  | after 2 Hrs. | 3.20 | 6.96 | 0.024 |
|  | after 15 Hrs. | 4.10 | 6.94 | 0.034 |
| Reference Example 3 | — | — | 6.99 | 0.018 |
| Example 3 | after 10 min. | 1.70 | 7.00 | 0.018 |
| Reference Example 4 | — | — | 7.14 | 0.041 |
| Example 4 | after 10 min. | 0.72 | 8.42 | 0.113 |
|  | after 30 min. | 1.60 | 8.36 | 0.171 |
|  | after 1 Hr. | 2.10 | 8.53 | 0.411 |
| Example 5 | after 10 min. | 0.07 | — | — |
|  | after 30 min. | 0.11 | — | — |
|  | after 1 Hr. | 0.17 | — | — |

Additional examples will be described hereinafter.

The hydrogen generating systems were obtained by mixing metal aluminum grains and calcium hydroxide with various compounding ratios. The obtained respective hydrogen generating systems contained metal aluminum grains and calcium hydroxide with weight ratio of 95:5 (Example 6), 90:10 (Example 7), 85:15 (Example 8), 80:20 (Example 9), 75:25 (Example 10), 70:30 (Example 11), and 65:35 (Example 12).

TABLE 2

|  | Left Time | DH (ppm) | pH | Al ion (ppm) |
|---|---|---|---|---|
| Reference Example 5 | — | — | 6.82 | 0.021 |
| Example 6 | after 10 min. | 1.00 | 7.00 | 0.046 |
|  | after 30 min. | 1.50 | 6.98 | 0.231 |
| Example 7 | after 10 min. | 2.10 | 7.13 | 0.164 |
|  | after 30 min. | 2.50 | 7.12 | 0.120 |
| Example 8 | after 10 min. | 2.50 | 7.23 | 0.068 |
|  | after 30 min. | 3.40 | 7.22 | 0.156 |
| Example 9 | after 10 min. | 2.50 | 7.34 | 0.044 |
|  | after 30 min. | 3.60 | 7.51 | 0.070 |
| Example 10 | after 10 min. | 2.50 | 7.18 | 0.040 |
|  | after 30 min. | 3.70 | 7.65 | 0.058 |
| Reference Example 6 | — | — | 6.93 | 0.024 |
| Example 11 | after 10 min. | 2.40 | 7.32 | 0.023 |
|  | after 30 min. | 3.80 | 7.74 | 0.020 |
| Example 12 | after 10 min. | 2.30 | 7.46 | 0.021 |
|  | after 30 min. | 3.80 | 8.12 | 0.022 |

DESCRIPTION OF REFERENCE NUMERALS a . . . separator
b . . . container
c . . . living organism applicable fluid
d . . . porous container

What is claimed is:

1. A method using an equipment for adding hydrogen into fluid applicable to a living organism comprising:
   providing a separator in which grains of metal aluminum as a hydrogen generating agent and at least either one of calcium oxide or calcium hydroxide as a hydrogen generating reaction accelerator are adjacently stored;

providing a closed container in which the fluid and the separator storing the grains of metal aluminum and at least the either one of calcium oxide or calcium hydroxide are stored,
wherein
   a fluid contained hydrogen is obtained by adding hydrogen gas into the fluid applicable to a living organism stored in the closed container, the hydrogen gas is generated by a contact reaction between the grains of metal aluminum and water,
   alumina cement is generated in the separator by a contact reaction among the grains of metal aluminum, the either one of calcium oxide or calcium hydroxide and water; and
   the alumina cement suppresses dissolution of aluminum ions into the fluid applicable to a living organism.

2. The method using the equipment as set forth in claim 1, wherein the separator includes a gas-permeable film which is made of a high molecular substance as a primary material.

3. The method using the equipment as set forth in claim 1, wherein the separator includes a gas-permeable film which is processed by water repellent finishing.

4. The method using the equipment as set forth in claim 1, wherein at least a part of the separator is held in an air space in the container.

5. The method using the equipment as set forth in claim 1, wherein the grains of metal aluminum and at least the either one of calcium oxide or calcium hydroxide are formed as a tablet or a solidified material.

\* \* \* \* \*